United States Patent [19]

Eckroat

[11] Patent Number: 4,936,326
[45] Date of Patent: Jun. 26, 1990

[54] DENTAL FLOSS CLEANING DEVICE

[75] Inventor: John D. Eckroat, Oklahoma City, Okla.

[73] Assignee: Elizabeth B. Eckroat, Oklahoma City, Okla.

[21] Appl. No.: 318,132

[22] Filed: Mar. 2, 1989

[51] Int. Cl.⁵ .............................................. A61C 15/00
[52] U.S. Cl. ...................................... 132/326; 132/323
[58] Field of Search ............... 132/321, 322, 323, 324, 132/325, 326, 327, 328, 329; 206/63.5

[56] References Cited

U.S. PATENT DOCUMENTS

| | | | |
|---|---|---|---|
| D. 251,075 | 2/1979 | Schiff | D28/64 |
| 1,287,926 | 12/1918 | Ecaubert | 132/325 |
| 1,468,942 | 9/1923 | Gamble | 132/324 |
| 1,623,231 | 4/1927 | Bowling et al. | 132/324 |
| 2,052,520 | 8/1936 | Sonnenberg | 132/324 |
| 2,163,500 | 6/1939 | Shepard | 132/326 |
| 2,756,758 | 7/1956 | Segerblom | 132/326 |
| 3,094,996 | 6/1963 | Lewis | 132/324 |
| 3,289,681 | 12/1966 | Chambers | 132/326 |
| 3,327,719 | 6/1967 | Ford | 132/326 |
| 3,376,876 | 4/1968 | Wicklund | 132/324 |
| 3,592,203 | 7/1971 | Johnson | 132/323 |
| 3,746,017 | 7/1973 | Casselman | 132/325 |
| 3,906,963 | 9/1975 | Jenkins et al. | 132/325 |
| 3,913,597 | 10/1975 | Day | 132/324 |
| 3,998,236 | 12/1976 | Koo | 132/324 |
| 4,495,957 | 1/1985 | Beggs et al. | 132/325 |
| 4,655,234 | 4/1987 | Bowden | 132/325 |
| 4,660,584 | 4/1987 | Wofford | 132/325 |

FOREIGN PATENT DOCUMENTS 2040686  9/1980  United Kingdom ............... 132/324

Primary Examiner—Gene Mancene
Assistant Examiner—Adriene B. Lepiane
Attorney, Agent, or Firm—Laney, Dougherty, Hessin & Beavers

[57] ABSTRACT

A dental floss cleansing device which includes a floss chamber connected by a neck to a bow frame spaced from the chamber. The bow frame includes a post projecting from a proximal end of an elongated shaft having a curved distal end. The shaft is centrally grooved for floss guiding purposes. A debris protective shield extends from opposite sides of the shaft over a major portion of its length. A floss strand extends from the floss chamber along the floss guiding groove in the shaft to the curved distal end of the shaft. The floss strand extends in a bight back to the post, and is there secured.

14 Claims, 1 Drawing Sheet

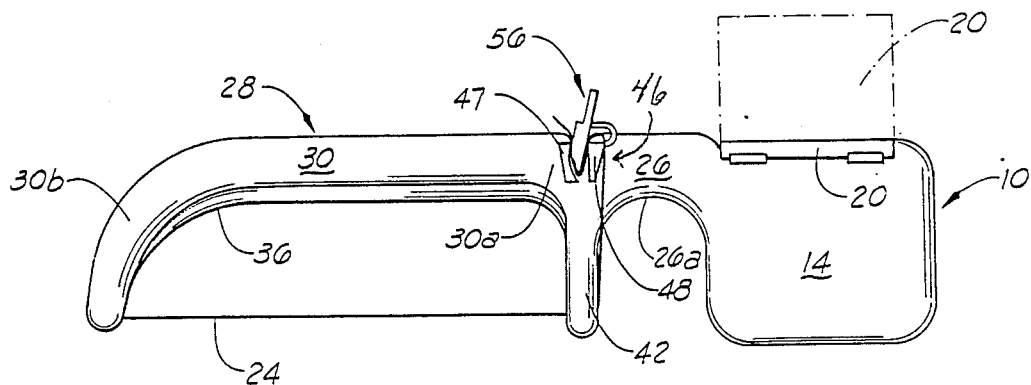
FIG. 1
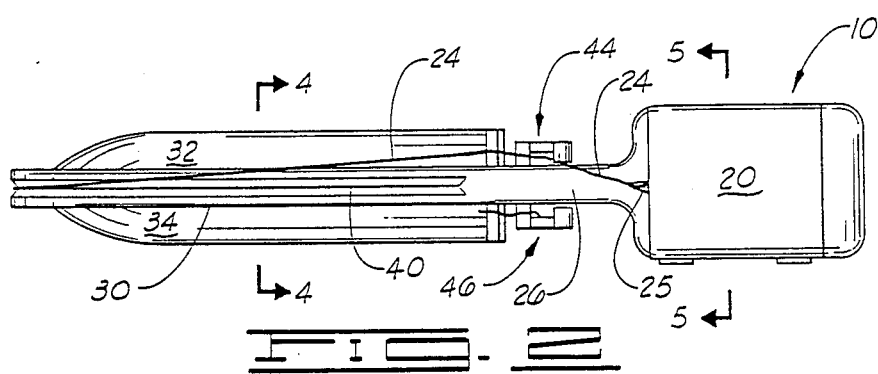
FIG. 2
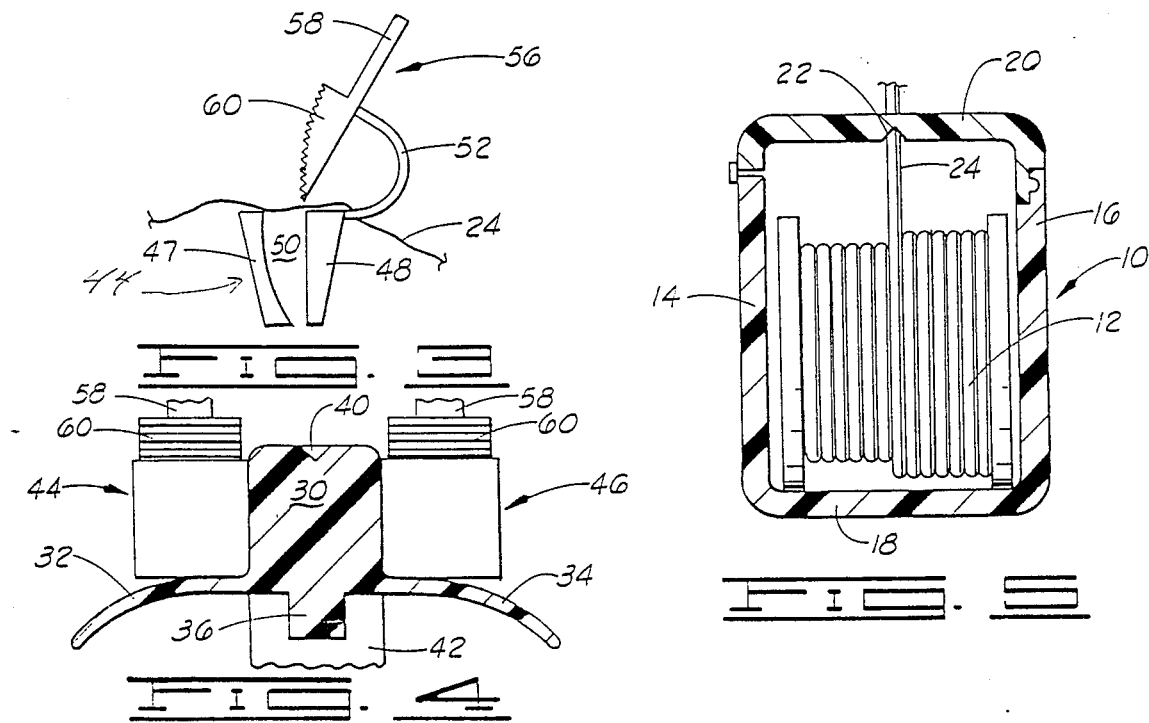
FIG. 3
FIG. 4
FIG. 5

DENTAL FLOSS CLEANING DEVICE

FIELD OF THE INVENTION

This invention relates to a dental floss cleaning device used for cleaning the teeth, and more particularly, to a device which includes a chamber for holding a supply of dental floss, and further includes, structure for exposing a taut span of the floss during cleaning of the teeth.

BACKGROUND OF THE INVENTION
BRIEF DESCRIPTION OF THE PRIOR ART

A number of types of dental floss holding devices have previously been provided which retain a strand of dental floss taut in the form of some type of bight or span in order to permit the device to be used to force the floss between the teeth and allow it to be worked back and forth in the cleaning operation.

In U.S. Pat. No. 3,289,681, issued to Chambers, a floss holding compartment or housing is provided on a dental floss cleaning device. This compartment has a hinged lid which permits the floss to be placed in a reservoir cavity. The floss is drawn from this location to a flossing span. After the floss is positioned to extend in a bight or span, it is clamped in this position by the use of ribbed protuberances which clamp on the floss.

A flossing span extended between a pair of posts or spaced structures is shown in Segerblom U.S. Pat. No. 2,756,758. The dental floss span is extended across from a leg of the device to a handle, and there is no space between such leg and handle to accommodate the lip and front teeth of the user of the device at the time when it is being used, and this makes it difficult to reach and clean the back teeth. In the Segerblom patent, no protective shield or canopy is provided which will protect the dentist, hygenist or technician against ricocheting or spattering material pried loose during the cleaning of the teeth.

Another U.S. patent having to do with devices for utilizing dental floss for cleaning teeth is Sonnenberg U.S. Pat. No. 2,052,520.

In U.S. Pat. No. 4,495,957, some finger actuated clamping levers are provided for holding the floss strand taut.

Yet another patent which has to do with dental floss holding and teeth cleaning devices include Wofford U.S. Pat. No. 4,660,584 which leads floss from a roll carried within a housing through an elongated shaft or arm, around an arcuate end portion and back through a bight or span.

Another dental floss holding tool is that which is illustrated in Bowden U.S. Pat. No. 4,655,234. The Bowden patent feeds the floss from a roll carried in a generally cylindrical housing out through a hollow shaft, around through an arcuate end portion and back to a post where the floss is stopped off. There is no space provided for the accommodation of the lip or front teeth of the user at a time when the back teeth are being cleaned, and the Bowden patent does not show any type of shield or protective canopy for preventing debris and saliva from leaving the mouth.

Other types of dental floss devices are shown in Schiff U.S. Pat. No. DES.-251,075, Lewis U.S. Pat. No. 3,094,996, Shepard 2,163,500, Bowling et al 1,623,231 and Ecauburt 1,287,926.

BRIEF DESCRIPTION OF THE PRESENT INVENTION

The present invention provides a dental floss cleansing device which includes a floss chamber which is connected by a neck to a bow frame, so that the bow frame is spaced from the chamber and provides a space therebetween to accommodate the lip and front teeth of the user of the cleaning device at a time when the back teeth are being contacted by the taut span of dental floss carried by the device.

The bow frame of the device includes a post which projects from a proximal end of an elongated shaft, with both forming parts of the bow frame. The shaft has a curved distal end which curves through about 90°. The shaft is centrally grooved along its length for guiding a strand of floss from a location adjacent the proximal end of the shaft where the floss strand is clamped, to a slot formed in the arcuate distal end of the shaft. A debris protective shield extends from opposite sides of the shaft over a major portion of its length. The floss strand extends from the floss chamber, along the floss guiding groove in the shaft, to the curved distal end of the shaft. From the curved distal end of the shaft, the floss strand extends in a bight back to the post, and it is is secured there by a suitable clamping mechanism.

The dental floss cleansing device made as described permits more efficient cleaning of the rear or molar teeth, and prevents debris and other solid material, as well as saliva, from being propelled out of the mouth of the person whose teeth are being cleaned.

An important object of the invention is to provide a dental floss cleansing device which can be relatively economically manufactured by molding it as an integral plastic unit, if such should be desired.

A further object of the invention is to provide a dental floss cleansing device which is especially well adopted for cleaning the rear teeth of the user, with minimal interference from the lips, cheek, gums and front teeth of the user.

A further object of the invention is to provide a shield to prevent debris, saliva and foreign material from being flung out of the mouth of the user in a way which interferes with the dentist, hygenist or technician who is cleaning the teeth of the patient.

Additional objects and advantages of the invention will become apparent as the following detailed description of a preferred embodiment of the invention is read in conjunction with the accompanying drawings, which illustrate such preferred embodiment.

GENERAL DESCRIPTION OF THE DRAWINGS

FIG. 1 is a side elevation view of the dental floss cleaning device of the invention.

FIG. 2 is a top plan view of the dental floss cleaning device.

FIG. 3 is a detail view illustrating a floss clamping element forming a part of the invention, showing the clamping element in side elevation.

FIG. 4 is a sectional view taken along line 4—4 of FIG. 2.

FIG. 5 is a sectional view taken along line 5—5 of FIG. 2.

DETAILED DESCRIPTION OF A PREFERRED EMBODIMENT OF THE INVENTION

The dental floss cleaning device of the invention includes a floss chamber designated generally by reference numeral 10 in which a roll 12 of dental floss can be located during use of the device. The floss chamber, as it is constructed in the illustrated embodiment, includes a pair of opposed side walls 14 and 16 and a bottom wall 18. The floss chamber 10 has an opening at the top thereof to facilitate the insertion of floss into the chamber, and this opening is closed by a hinged lid 20 which is shown in the closed position in FIG. 5. In FIG. 1, the lid 20 is illustrated by dashed lines as it appears in its open position. A small slot or groove 22 is formed in one side of the lid 20 to permit the floss strand 24 to be pulled out of the floss chamber 10, and positioned in the device in the manner hereinafter described.

A neck 26 is connected to one side of the floss chamber 10 and interconnects the floss chamber to a bow frame designated generally by reference numeral 28. For a reason hereinafter described, the neck 26 has a curved or arcuate concave lower surface 26a located between the floss chamber 10 and the bow frame 28, as illustrated in FIG. 1. The bow frame 28 includes an elongated shaft 30. The shaft 30 has a proximal end 30a located adjacent and connected to the neck 26, and an arcuate, distal end 30b at the opposite end of the shaft. The arcuate distal end includes a portion formed on a radius and defining an angle of 90° with the longitudinal axis of the shaft.

At its outer lower side edges, the shaft 30 has formed integrally therewith, a pair of outwardly extending, arcuately configured flanges 32 and 34 which together form a protective shield or canopy to prevent debris and particles of food and saliva from flying out of the mouth in which the dental floss device is being used. This protective function of the shield or canopy is one of the most important features of the invention since, at the present time, for fear of AIDS, hepatitis, etc., and other infectious diseases, dentists and hygienists, if prudent, wear eye glasses, rubber gloves and masks to protect themselves against flying debris, particles of blood and saliva as they use floss to clean the teeth of patients. The canopy also functions to prevent mirrors in use during the flossing of teeth from becoming fouled and soiled by flying debris. Centrally located beneath the elongated shaft 30 is an elongated support strut or rib 36. The support strut or rib 36 extends over a major portion of the shaft 30, as illustrated in FIG. 1, and is merged into the shaft at its opposite ends. An elongated groove or channel 40 extends along the upper side of the shaft 30 from one end thereof to the other, and follows a portion of the arcuate distal end portion 30b of the shaft.

A floss guide post 42 projects downwardly from the proximal end of the shaft in a direction substantially normal to the longitudinal axis of the shaft. The floss guide post 42 has a slot (not visible) formed in the lower end thereof through which a strand of the floss can be extended for a purpose hereinafter described.

A pair of floss latching subassemblies, designated generally by reference numerals 44 and 46, are provided on opposite sides of the shaft 30 at the proximal end thereof. The floss latching subassemblies are positioned in substantially horizontal alignment with the upper side of the shaft, as shown in FIGS. 1 and 4. Each of the floss latching subassemblies 44 and 46 includes a pair of wedge engaging plates 47 and 48 which are secured to, or formed integrally with, the opposite sides of the shaft. The wedge engaging plates 47 and 48 are spaced from each other so as to define an intervening space or slot 50. It will be noted in referring to FIG. 3 that the wedge engaging plate 47 has a concave inner side.

Secured by a flexible strap or web 52 to the respective sides of the wedge engaging plate 48 which face toward the floss chamber 10 is a wedge latch 56. The wedge latch 56, which is identically constructed in the case of each of the floss latching subassemblies 44 and 46, includes a projecting finger grip portion 58, and a serrated or toothed wedge portion 60. The wedge portion 60 has a convex side which faces the concave side of the wedge engaging plate 47 and carries the serrations. The wedge portion 60 can be wedged into the space 50 so that its teeth on the convex side thereof engage the concave side of the wedge engaging plate 47. Movement of the wedge latch 56 is facilitated by the flexible strap or web 52 which connects the latch to the outer side of the wedge engaging plate 48.

USE AND OPERATION

In the use and operation of the dental floss holder device of the invention, a roll 12 of dental floss is first placed into the floss chamber 10 by opening the pivoted lid 20 and dropping the roll of floss into the floss chamber. The lid is then re-closed after a free end of the floss has been pulled out and leaves the floss chamber at a location adjacent the lid 20, so that the floss strand can be guided by the slot or groove 22 formed on the inner edge of the lid 20 near one side thereof.

After the floss strand 24 has been pulled out of the floss chamber 10, it is led across the floss strand latching subassembly 44 into a position such that it extends above the space 50 formed between the wedge engaging plates 47 and 48. This relationship is shown in FIG. 3.

When the floss strand has been pulled across the wedge engaging plates 47 and 48 in the manner shown, the finger plate 58 is then grasped, and the serrated wedge portion 60 is wedged downwardly into the space 50. This forces the strand 24 of floss into the space 50 between the wedge engaging plates 47 and 48, and as the wedge latching member 56 is forced into position, the wedge portion 60 engages the floss strand and forces it against the wedge engaging plate 47.

Before the strand of floss has been stopped off and secured in the floss strand latching subassembly 44 in the manner described, the floss strand has been pulled through in sufficient length to reach through the entire extent of the path that is to be followed by it through the apparatus. The strand of floss is then led into the groove or channel 40 which extends in a longitudinal direction along the upper side of the shaft 30 as shown in FIGS. 2 and 4.

At the distal end of the shaft 30, the strand of dental floss passes through a central guide slot (not illustrated), and an elongated, taut bight of the floss strand 24 is extended to the downwardly projecting post 42 as illustrated in FIG. 1. The strand 24 of the floss is then pulled through a slot (not visible) at the bottom of the post 42 and is pulled upwardly. It is finally pulled across the wedge engaging plates 47 and 48 of the latching subassembly 46. The wedge latching member 56 is then forced downwardly so as to trap the strand of floss 24 between the wedge engaging plates 47 and 48, and thus lock the floss in a taut status.

The dental floss cleaning device of the invention is then utilized by gripping the floss chamber 10 with the fingers and extending the bow frame 28 into the mouth until the bight portion of the floss strand 24, which extends between the end of the shaft 30 and the post 42, passes between teeth to perform the usual cleaning function. In the case of the rear molars of the patient or person using the floss, the space defined between the post 42 and the floss chamber 10, and the accommodation of the teeth and gums by the arcuate lower surface 26a of the neck 26, allow the device to pass over the front teeth and lip at the front of the mouth, and prevents interference from occurring between the front teeth and the device as the molars are cleaned.

It is often necessary to extend the dental floss cleaning device laterally into the mouth, and substantially normal to the jaw area, in order for the bight portion of the floss strand to reach, and be extendable between, molar teeth within the mouth, particularly on the opposite side of the mouth of the patient. In this case, the space between the post 42 and the floss chamber 10 functions to accommodate the cheek and lip of the patient on the side of the mouth from which the dental floss cleaning device is being extended into the mouth.

As the teeth in the mouth are being cleaned, the zone immediately adjacent the patient's mouth is protected from ricocheting debris and saliva which might be thrown from the mouth during the cleaning operation by the shield or canopy formed by the dual outwardly extending flanges 32 and 34. These flanges, of course, extend broadly across the line of the bight portion of the floss strand 24, and thus protectively overlie the zone of cleaning of the teeth.

Although a preferred embodiment of the invention has been herein described in order to clearly illustrate the principles of the invention, various changes and innovations in the described structure can be effected without departure from these basic principles. Changes and innovations of this type are therefor deemed to be circumscribed by the spirit and scope of the invention except as the same as may be necessarily limited by the appended claims or reasonable equivalents thereof.

What is claimed is:

1. A dental floss tooth cleansing device for safely and sanitarily cleaning teeth without exposure to flying debris, blood and saliva comprising:
   a hollow floss chamber forming a handle;
   a lid hinged to the upper part of the floss chamber;
   a neck;
   a bow frame connected to said floss chamber by said neck, said bow frame including:
      an elongated shaft having a proximal end connected to said neck, and having a distal end, said shaft having an upper side, a lower side and a floss groove extending along at least a portion of the upper side thereof;
      a pair of laterally extending flanges extending outwardly from said shaft on the opposite sides of the longitudinal center line of said shaft and extending over a major portion of the length of said shaft; and
      a post projecting from said shaft at a location adjacent the proximal end thereof; and
   a strand of dental floss extending from said floss chamber into said floss groove, around said distal end and back to said post to define an exposed bight of dental floss between the shaft distal end and said post;
   said laterally extending flanges lying on each of the opposite sides of a plane extending through, and including the longitudinal center line of said shaft and said exposed bight of dental floss, to thereby form a canopy shielding said exposed bight of dental floss and preventing particles of blood, debris and saliva from being flung out of the mouth of the patient as the dental floss is used and thereby substantially reducing the danger of contamination of a person utilizing the dental floss tooth-cleansing device.

2. A dental floss tooth cleaning device as defined in claim 1 and further characterized as including floss latching means connected to said shaft adjacent the proximal end thereof for securing said strand of dental floss at two points spaced therealong on opposite sides of said exposed bight.

3. A dental floss tooth cleaning device as defined in claim 2 wherein said floss latching means comprises a first floss latching subassembly secured to said shaft on one side thereof, and a second floss latching subassembly secured to said shaft adjacent the location where the post is joined to the shaft.

4. A dental floss tooth cleansing device as defined in claim 1 wherein said bow frame is spaced from said chamber by a distance sufficient to accommodate therein the canine or incisor teeth and lip of a user of the device when using the device to clean the molar teeth.

5. A dental floss tooth cleansing device as defined in claim 4 wherein said neck extends across said distance between the chamber and the bow frame, and interconnects the upper side of said shaft and one side of said chamber, and wherein said neck has a rounded, concave lower side.

6. A dental floss tooth cleansing device as defined in claim 1 and further characterized as including a reinforcing rib extending along and secured to the underside of said shaft.

7. A dental floss tooth cleansing device comprising:
   a floss chamber;
   a neck;
   a bow frame connected to said floss chamber by said neck, said bow frame including:
      an elongated shaft having a proximal end connected to said neck, and having an arcuate distal end, said shaft having an upper side, a lower side and a floss groove extending along at least a portion of the upper side thereof;
      a pair of laterally extending flanges extending outwardly from said shaft on the opposite sides of the longitudinal center line of said shaft and extending over a major portion of the length of said shaft; and
      a post projecting from said shaft at its location adjacent the proximal end thereof; and
   a strand of dental floss extending from said floss chamber into said floss groove, around said distal end and back to said post to define an exposed bight between the shaft distal end and said post;
   floss-latching means connected to said shaft adjacent the proximal end thereof for securing said strand of dental floss at two points spaced therealong on opposite sides of said exposed bight, said floss-latching means comprising:
      a first floss-latching subassembly secured to said shaft on one side thereof; and
      a second floss-latching subassembly secured to said shaft adjacent the location where the post is joined to the shaft;
   each of said floss-latching subassemblies comprising:
      a pair of spaced wedge engaging plates;

a flexible strap; and a wedge latch secured to the flexible strap and insertable into the space between said wedge-engaging plates.

8. A dental floss tooth cleansing device as defined in claim 7 wherein said bow frame is spaced from said chamber by a distance sufficient to accommodate therein the canine or incisor teeth and lip of a user of the device when using the device to clean the molar teeth.

9. A dental floss tooth cleansing device as defined in claim 8 wherein said neck extends across said distance between the chamber and the bow frame, and interconnects the upper side of said shaft and one side of said chamber, and wherein said neck has a rounded, concave lower side.

10. A dental floss teeth cleaning device comprising:
a floss chamber;
a neck having a rounded, concave lower side and an upper side;
a bow frame connected to, and spaced from, said floss chamber by said neck, said bow frame including:
an elongated shaft having a proximal end adjacent and connected to said neck, and an arcuately configured distal end spaced from said neck, said arcuate distal end being slotted;
a post extending substantially perpendicularly to the longitudinal axis of said shaft and projecting from said shaft at a location adjacent the proximal end thereof;
a pair of floss-latching subassemblies connected to said shaft adjacent the proximal end thereof, each of said latching subassemblies comprising:
a pair of spaced wedge-engaging plates;
a flexible strap; and
a wedge latch secured to the flexible strap and insertable into the space between said wedge-engaging plates; and
a strand of floss extending from said floss chamber to a point at which said strand is engaged by one of said floss-latching subassemblies, and from one floss-latching subassembly along said shaft and through the slot in the arcuate distal end of said shaft and from said slot to said post, and from said post to a point at which said strand is engaged by the other of said floss-latching subassemblies.

11. A dental floss teeth cleaning device as defined in claim 10 wherein said elongated shaft has an upper side and a lower side, said upper side having a groove therein extending parallel to the longitudinal axis of said shaft; and
wherein said cleaning device further includes a reinforcing rib extending along the lower side of said shaft.

12. A dental floss teeth cleaning device as defined in claim 10 wherein said cleaning device is a single, integral unit of synthetic resin.

13. A dental floss teeth cleaning device as defined in claim 10 wherein said floss chamber is a chamber of generally rectangular parallelepiped configuration having a lower side, and upper side and an opening thereinto; and
wherein said device further includes a hinged lid closing the opening into said chamber.

14. A dental floss cleansing device for safely and sanitarily cleaning teeth without exposure to flying debris, blood and saliva, said cleansing device being constituted by a single, integral synthetic resin molded unit, and said cleansing device further comprising:
a floss chamber of generally rectangular parallelepiped configuration having a lower side, an upper side and an opening thereinto;
a hinged lid joined to an upper portion of said floss chamber and movable to a position closing the opening into said floss chamber;
a neck portion projecting from the upper portion of said floss chamber, said neck portion including:
a rounded, arcuate, lower side adapted to contact the lip of the patient without cutting or abrading the skin;
a bow frame connected to said neck portion on the opposite side thereof from said floss chamber and connected by said neck portion to said floss chamber, said bow frame including:
an elongated shaft extending from said neck portion and terminating in an arcuate distal end spaced from said neck portion; and
a post extending perpendicularly to the longitudinal axis of said elongated shaft at a location adjacent said neck portion and defining with said neck portion and said floss chamber, a space for accommodating the lip of a user when the back molar teeth are being cleaned, and the floss chamber is used as a handle to hold the cleansing device; and
means for stretching a strand of dental floss in a bight extending tautly between the distal end of the shaft and said post, said bight extending substantially parallel to the longitudinal axis of said shaft, said stretching means comprising:
a first finger-operable, floss-latching subassembly secured to said shaft on one side thereof adjacent said neck portion for latching and securing said strand of dental floss at the location of said first finger-operable floss-latching subassembly on one side of said bight between the bight and the floss chamber, said first finger-operable floss-latching subassembly being operable for latching the floss and securing it at the location of said first latching subassembly by one of the fingers of the user of the device while the user is concurrently gripping the floss chamber as a handle; and
a second finger-operable floss-latching subassembly secured to said shaft adjacent the location where the post is joined to the shaft, and engageable with a strand of dental floss after the strand has been extended through said bight, said second finger-operable floss-latching subassembly being operable by one of the fingers of the user of the device while the user of the device uses the same hand carrying the finger for gripping the floss chamber as a handle and using the device; and
a shield and canopy means extending outwardly from opposite sides of the shaft at a position to protect one using the device, from flying debris and particles at a time when the device is being used.

* * * * *